(12) United States Patent
Ward et al.

(10) Patent No.: US 8,597,937 B2
(45) Date of Patent: Dec. 3, 2013

(54) REACTION APPARATUS (75) Inventors: David Ward, Guisborough (GB); David Edge, Warlingham (GB); Nelson Nazareth, Upper Dean (GB)

(73) Assignee: BG Research Ltd, Cambridgeshire (GB)

( * ) Notice: Subject to any disclaimer, the term of this patent is extended or adjusted under 35 U.S.C. 154(b) by 922 days.

(21) Appl. No.: 12/381,953

(22) Filed: Mar. 18, 2009

(65) Prior Publication Data

US 2009/0263782 A1 Oct. 22, 2009
US 2012/0077183 A9 Mar. 29, 2012

Related U.S. Application Data (63) Continuation of application No. PCT/GB2007/003564, filed on Sep. 18, 2007.

(30) Foreign Application Priority Data

Sep. 19, 2006 (GB) .................................. 0619128.2
May 29, 2007 (GB) .................................. 0718250.4

(51) Int. Cl.
*C12M 1/34* (2006.01)
(52) U.S. Cl.
USPC .................... 435/287.2; 435/91.2; 435/303.1

(58) Field of Classification Search
USPC ............................... 435/3, 91.2, 287.2, 303.1
See application file for complete search history.

(56) References Cited

U.S. PATENT DOCUMENTS

| | | | |
|---|---|---|---|
| 2002/0072112 A1* | 6/2002 | Atwood et al. | 435/303.1 |
| 2003/0106682 A1* | 6/2003 | Reid et al. | 165/206 |
| 2003/0165941 A1* | 9/2003 | Gjerde et al. | 435/6 |
| 2004/0038390 A1* | 2/2004 | Boege et al. | 435/288.7 |
| 2005/0036667 A1* | 2/2005 | So et al. | 382/128 |

FOREIGN PATENT DOCUMENTS

WO WO01/37997 A1 * 5/2001

* cited by examiner

*Primary Examiner* — Michael Hobbs
(74) *Attorney, Agent, or Firm* — J. Bruce Hoofnagle

(57) ABSTRACT

An apparatus 20 for biological or chemical reactions, in particular PCR, includes a heat removal module 22 adapted to receive snugly a reaction vessel 24 in such a manner as to create good thermal conductivity contact between the module and the vessel. The heat removal module 22 is formed of a thermally conductive material having therein a channel 64 adapted for the flow of a coolant liquid. The heat removal module 22 is constructed with an array of receiving stations 62 for the reception of a corresponding array of reaction vessels 24.

24 Claims, 6 Drawing Sheets

…

REACTION APPARATUS

This application is a continuation of International Application No. PCT/GB2007/003564, filed on Sep. 18, 2007, which, in turn, claims the benefit of UK applications GB 0619128.2, filed on Sep. 19, 2006, and GB 0718250.4, filed on May 29, 2007, all three of which are incorporated herein by reference thereto.

FIELD OF THE INVENTION

This invention relates to apparatus for biological or chemical reactions where thermal cycling is employed in the reaction. It is particularly concerned with reactions such as polymerase chain reactions (PCR).

The PCR process is described in detail in U.S. Pat. No. 4,683,195, which issued on Jul. 28, 1987, and U.S. Pat. No. 4,683,202, which issued on Jul. 28, 1987.

BACKGROUND OF THE INVENTION

Typically a large number of reduced volume reactions are carried out simultaneously in one apparatus, with a plurality of reaction vessels being received in a reaction apparatus at one time. Often the reaction vessels are in the form of a tray, known as a microtiter plate, made up of an array of vessels. In one standard microtiter plate, 96 vessels are formed in one array. In order to control and monitor the reactions, the apparatus includes means to monitor the temperature and to control the heating power applied to the reaction vessel contents.

Often, in reactions involving multiple thermal cycles, the cooling part of the cycle is effected using a cooling block and/or a fan blowing cooled air over the vessel or vessels. Often the cooling is continuously present and the heating part of the cycle is carried out against a background of the cooling. Thus, for example, in conventional block thermal cyclers, heating is effected using a direct heater, for example thermal mats, and cooling by either forced air or actively by thermo electric heat pumps. In other thermal cycling apparatus, heating and cooling are effected by shuttling between blown hot air and blown cold air.

There are situations, for example, when it is required to identify what may be a dangerous pathogen, in which it is highly desirable to minimize the time taken by such a reaction. Apparatus for minimizing the time required in the heating part of the cycle is described in UK Patent Nos. GB 2404883B, published on Feb. 27, 2006, and GB 2424380B, published on Jun. 27, 2007, both of which are incorporated herein by reference thereto. In this apparatus, an electrically conductive polymer is employed as, or as part of, the material of the reaction vessel. Cooling is effected using forced cooled or ambient air.

Normally, the maximum cooling rate achievable using forced air is 8° C. per second. A higher cooling rate than this would be very useful. The present invention provides means whereby cooling in biological or chemical reactions requiring thermal cycling is significantly accelerated.

SUMMARY OF THE INVENTION

According to the present invention, an apparatus for biological and chemical reactions includes a heat removal module adapted to receive snugly a reaction vessel in such a manner as to create good thermal conductivity contact between the module and the vessel, the module being formed of a thermally conductive material having therein a channel adapted for the flow of a coolant liquid.

The coolant liquid may be water, preferably deionized water with an antioxidant addition. A typical example of such a coolant liquid is FluidXP+, which is supplied by Integrity PC Systems & Technologies, Inc. of Riverdale, Calif. USA.

Typically, thermo-cycling reaction apparatus is arranged to receive in stations a standard array of 96, or an integer multiple thereof, microtiter reaction vessels in a rectangular array, usually comprising 12 by 8 such stations.

According to a feature of the present invention the heat removal module may comprise a single block of thermally conductive material arranged to provide an array of receiving stations for microtiter reaction vessels and the channel is in labyrinthine form whereby the coolant liquid flows adjacent each receiving station and each reaction vessel.

It has been found that with a heat removal module according to the present invention a mean vessel cooling rate of 18° C. per second can be achieved, with a peak of 24° C. per second.

In one embodiment, the heat removal module is formed of two mating plates and the channel is formed in one plate or in mating surfaces of both plates, for example, by milling or routing. When fitting the two plates together, a suitable sealant may be used between two interfacing surfaces of the plates to ensure no escape of the coolant liquid. The sealant may also be required to insulate one plate from the other electrically.

In another preferred embodiment, the heat removal module is formed of a single block and the channel is formed by drilling through the block, and then blocking any unwanted exits or routes using stoppers such as grub or set screws.

The material of the block is composed of any one, or combination, of copper, aluminum alloy, silver, or gold, boron nitride, diamond and graphite among the possibilities.

In a preferred context, where the vessel incorporates heating means, for example, it includes an electrically conductive polymer (ECP), the module may be arranged to provide a path in the electrical circuitry. In such a case it may be advantageous for the module to be coated, where necessary, with an electrical insulation material. For example, it may be anodized.

Where the heating of each vessel is to be individually controlled then, given the space constraints of a microtiter array, the heat removal module may be adapted to receive contact elements for the supply of electric current while acting as the return contact element, or vice versa. The contact elements may be formed of beryllium, copper, or a woven polyester coated or plated with copper and/or nickel. Since the heat removal module may be located on a printed circuit board (PCB), which includes electrical contact elements, a jig may be constructed to ensure that the electrical contact elements will attach to the PCB so as to fit non-interferingly in recesses formed in the module.

Where the heating is not obtained by using the vessel, or part thereof, as the heating element, the heat removal module may be adapted to receive the heating element(s). A heating element such as a Peltier cell may be employed in this situation.

Fortunately it is usually the case that the lower temperature required in biological or chemical reactions involving thermo-cycling is higher than ambient. Often it is anyway necessary that the lower temperature is as precisely controlled as the upper temperature. Accordingly, apparatus for effecting such reactions, and incorporating a heat removal module according to the invention, may also have a heater for heating the coolant liquid to the desired temperature. This has the added advantage of preventing condensation from forming on the exterior of the heat removal module.

The standard pitch of microtiter reaction vessels in a 12 by 8 array is 9 mm. The bore of the channel may be of the order of 3 mm.

A reaction vessel, particularly suitable for use in a heat removal module according to the invention, is described in the above-noted UK Patent GB 2404883B and comprises a working or reaction portion 8 mm long with a mean bore of 2.5 mm, a contact portion of approximately 4 mm outside diameter and 3 mm length and a funnel-like portion of 6 mm mean outside diameter and 7 mm length. The vessel is formed of electrically conductive material with an electrically insulated plastics liner. The electrically conductive material may comprise a carbon based filler such as Buckminster fullerine tubes or balls, carbon flake or powder within a polypropylene matrix. Typically, the carbon content is up to 70% by weight, with 10% being carbon black and the rest graphite. The total wall thickness of the vessel is of the order of 0.3 mm. The base of the vessel has a toroid formed thereon to accommodate a temperature sensing device, which may be of the thermal contacting type, for example a thermistor, or the remote sensing type, for example a thermopyle type. A lid fits into an open end of the funnel-like portion and the contact portion of the vessel and seals the vessel when in use. The lid has a window at the base thereof immediately above the working portion of the vessel, and facilitates optical interrogation of the reaction process.

The module may however be constructed for use with a vessel of a different form, including a BioChip.

According to a second aspect of the invention, a reaction apparatus, in which one or more reaction vessels are received and the reactions therewithin monitored, includes one or more vessel receiving stations each for receiving a reaction vessel and, for each receiving station, a method of thermometry of the reaction vessel. This may comprise contact thermometry or infra-red detection.

In the case of infra-red detection, each receiving station may have a thermopile sensor. If necessary, there may also be a heat guide arranged to collect heat radiated from the surface of the vessel and to guide it onto the sensor. This can avoid having to ensure that the sensor is exactly aligned normal to the surface of an adjacent station and vessel. Typically, the heat guide is formed of aluminum, copper, or another material with low emissivity and high reflectivity arranged to reflect the heat radiated from the vessel onto the thermopile.

Preferably such thermopile sensors are mounted upon a PCB including bores through which the reaction vessels pass. The PCB and the heat guide may be formed with small openings, including bores larger than the local diameter of the vessel, to allow the passage of a cooling gas such as air.

This provides an extremely robust, reproducible and non-invasive means of measuring and/or controlling the temperature of individual reaction vessels independently of the other reaction vessels within the reaction vessel matrix. Typically the distance of the thermopile sensor to the vessel is between 0.5 mm and 30 mm. In the context of microtiter vessels having a maximum diameter of 1 cm, this distance is under 1 cm. Where the location of such a sensor is impossible due to space restrictions, a thermal guide such as a glass fiber strand/optical fiber may be used as a waveguide to transport the infra-red energy to a remote sensor.

Advantageously, the outer layer of the vessel is highly thermally emissive to provide a vessel having as close as possible to black body external surface properties. This is particularly suited to systems where non-contact temperature measurement is required. Where highly thermally emissive materials cannot be used, the difference between perfect and actual emissivity may be used to derive the correct temperature of the vessel and the contents thereof.

Where thermally emissive materials are not available, or non-contact thermometry is not suitable, contact thermometry may be used to derive the temperature of the vessel. Such a contact temperature sensor is preferably sited other than at actively heated or cooled portions of the vessel. A thermally conductive material duct may, if desired, be employed between the vessel and the sensor.

It is usually the case that the vessel is sealed with the lid, or a cap, for the duration of a reaction and such a lid may be translucent or even transparent for at least a part thereof to form a window adjacent the reaction sample, whereby the progress of the reaction can be monitored. According to features of the invention, such a lid may be provided and may be arranged so that the window is heated to slightly above sample temperature and leaves only a minimal, if any, air gap above the sample. This feature, and/or heating the window, serves to prevent condensation on the window, enable rapid temperature rise in the sample, and prevent concentration of the sample by evaporation. Advantageously, the lid has a low thermal mass to allow it to be heated and cooled as quickly as possible.

In an alternative construction, such lids or caps are made of a thermally conductive material and heated individually to a thermal profile in a manner to encourage the condensation in the vessel to evaporate during an optical detection process, and cooled when optical detection is not required to encourage the condensate to collect on the lid and drip into the vessel. Alternatively, the lid may be held at a constant temperature to minimize evaporation that might cause concentration of the reaction within the vessel.

Preferably the vessel is arranged to contain the entire sample in a minimally tapered cylinder at a lower section of the vessel, with the taper angle being chosen for the optical application and ease of molding if the vessel is produced by a molding method. Typically, the taper angle is of the order of 1-6° and the thickness of the outer layer is between 0.01 and 1 mm. The taper has the advantage of permitting air above the sample to escape when the lid is being located on the vessel.

In order for the maximum heat transfer to be able to take place as effectively as possible, the tube shape of the vessel should have as large a surface area to volume ratio as possible. The ideal shape would be to have the fluid held between two plates of ECP that would be heated and cooled. However, this design does not lend itself to molding with ECP, and neither does it lend itself to being locatable in a 96 well microtiter plate (MTP) format in a 9 mm square vessel array context. However, it may be suitable with a non-microtiter vessel context, for example a BioChip.

Inside this footprint, the ideal vessel reaction chamber has substantially capillary dimensions and a high aspect ratio. As thin a wall thickness as is possible for ready and reproducible moldability and safe handling has advantages then in terms of heat transfer and material costs. Consequently, the wall thickness may be between 0.1 mm and 2 mm.

The ability to transfer heat into and out of the reaction vessel is directly proportional to the wall thickness of the reaction vessel in contact with the heating or cooling medium. Doubling the wall thickness will double the thermal gradient required to transfer the same amount of energy into the reaction vessel. The higher the ratio of surface area to volume ratio the better the results. Preferably, the ratio of surface area to volume is above 3 and preferably above 6.

Preferably, the reaction vessel is constructed for use in apparatus with the base of the vessel and an upper edge portion of the outer heating layer thereof providing electrical contact areas.

According to yet another feature of the invention, an optical monitoring system for a reaction apparatus may be provided, where the reaction apparatus defines a plurality of receiving stations, each such station receiving a reaction vessel in which a reaction may take place.

The optical monitoring system may comprise at least one radiation source. Also provided is a scanning apparatus for directing radiation to vessels in the receiving stations, and for directing radiation emitted by the reaction vessel contents into photometric apparatus. The photometric apparatus directs received radiation to a diffraction grating or equivalent technology, and thence to a photomultiplier tube assembly, preferably operating in a photon counting mode.

The photomultiplier tube assembly may comprise a series of single channel multi-anode photomultiplier tubes, but preferably the assembly comprises a multi-channel multi-anode photomultiplier tube (MAPMT).

Radiation emitted by the vessel contents is dispersed over the pixels of the MAPMT by use of a diffraction grating such that the range of wavelengths of radiation impinging upon a photocathode of the MAPMT correlates with the position of the photocathode in the MAPMT.

In one embodiment, the MAPMT is a 32 pixel linear array over which radiation from around 510-720 nm is dispersed. Thus, the optical monitoring system provides for the use of a broad range of fluorophores emitting radiation at wavelengths between about 510 nm and about 720 nm without the need to change filter sets as required in other instrumentation.

The use of the MAPMT, and operating it in photon counting mode, provides for sensitive detection of radiation, thereby facilitating the measurements of low levels of incident fluorescence associated with high sampling frequencies. Measurements using a MAPMT, operating in photon counting mode, are less affected by changes in the electromagnetic environment, than if the MAPMT is operated in analog mode.

The optical monitoring means is preferably an integral part of the reaction apparatus.

Preferably, the light source is a single light source, typically a laser, and the laser is a diode pumped solid-state laser (DPSSL) in contrast to the gas lasers used in conventional reaction apparatus and optical monitoring systems.

Preferably means are provided for monitoring the reactions within a plurality of vessels, by directing radiation from a single excitation source to the vessels, and collecting the resultant radiation from the vessels to be measured by a single photometric system. Such a means may comprise one or more rotatable mirrors, where the configuration of mirrors can be controlled to direct light to and from any specific vessel. An array of two mirrors is preferred. The size and bulk of the mirror is arranged to be such as to achieve efficient radiation collection with minimum scanning frequency.

The use of a single excitation source and a single photometric system in the same way for all vessels under observation reduces the possibility of variability being introduced into measurements due to the differences between multiple detectors or sources of excitation. In addition, it facilitates the cost-effective use of high quality components in excitation and detection sub systems. This is particularly suited for use with high quality photomultiplier systems The acquisition of a full spectrum from each vessel at each sampling point facilitates the concurrent use of multiple different fluorophores in the array of reaction vessels in the apparatus (including use of multiple different fluorophores within a single vessel) as required by some fluorometric applications. Such a spectrum may also be acquired in a single operation reading all channels of the MAPMT concurrently, in contrast to systems where readings at different wavelengths must be acquired consecutively, for example by use of a filter wheel or other means. This technique affords higher sampling rates, and removes effects related to variation in signal between the acquisitions of different wavelengths.

A Fresnel lens may be used in the path of the laser, and is light, cost-effective and very compact compared to a standard lens of the same diameter and optical properties. The Fresnel lens ensures that the radiation from the excitation source is always directed substantially vertically when it enters each vessel. The rotating mirrors cause the beam to be reflected at an angle, such that it hits the Fresnel lens at a point above the vessel to be illuminated, the Fresnel lens refracts the beam from this point to enter the vessel vertically. The resultant emitted radiation from the vessel is refracted from vertical travel to the correct angle to return to the rotating mirrors and hence to the photometric system.

A plurality of light sources may be used as the excitation source to illuminate the sample with a variation of radiation spectra. The excitation sources may be a plurality of individually attenuated lasers, a plurality of Light Emitting Diodes, a Light Emitting Diode (LED) capable of generating a variety of spectra (RGB LED's) or multiple incandescent or fluorescent lamps.

Software and/or physical filters may be used to remove incident light from the detected sample spectra and also to remove emissions resultant from excitation from one source from those resultant from another source, and in this way allow non source-specific emissions to be subtracted and experimentally link fluorophores in the reaction to specific light sources as discussed above. This allows the apparatus to excite at a number of individual wavelengths simultaneously while removing the necessity to change filters using a filter wheel. Where single excitation sources are used, a physical filter may be used to remove the excitation spectra from the detected sample spectra. Filter Wheels are generally regarded as slow devices capable of performing several color changes per second. The use of the software filtering allows up to 1500 samples per second to be filtered. Regarding detection, CCD, a photomultiplier tube or an avalanche photo diode array are among the possibilities.

An alternative optical monitoring system comprises a PCB located above the reaction vessels, with the PCB holding an array of LEDs selected so as to be within the excitation spectrum of the vessel contents under interrogation and arranged for the direction of light into the vessel. The PCB also has a plurality of small openings arranged to permit the passage of a light emission spectra from the content of each vessel. The system also includes detector apparatus arranged to detect the emission spectra and filter means to block the path of excitation spectra to the detector.

Preferably the LEDs are arranged to emit light at the blue end of the optical spectrum, typically at a wavelength of 470 nm or above. One suitable detector apparatus may comprise a Fresnel lens arranged to direct the light onto an XY scanning mirror set and thereby into a detector such as a PMT, APD (avalanche photo-diode), CCD (charge couple device), LDR (light dependent resistor) or a photovoltaic cell. The PMT may be single cell or, if the emission beam is split into a spectrum, an array thereof. The filter means may include an optical filter placed, for example, across the small opening, or software associated with the detector. With the lid usually covering the vessel, the optical monitor system is arranged for light path association therewith.

BRIEF DESCRIPTION OF THE DRAWINGS

Embodiments of the invention will now be described, by way of example only, with reference to the accompanying drawings, in which.

DETAILED DESCRIPTION OF THE PREFERRED EMBODIMENTS

Referring to FIGS. 1, 2, 3 and 4, in accordance with certain principles of the invention, an apparatus 20, for biological and chemical reactions, includes a heat removal module 22 (hereinafter "the module") formed from a heat conductive material. In addition, the material which forms the module 22 is electrically conductive, and may be selected from any one material, or combinations thereof, consisting of copper, aluminum alloy, silver, gold, boron nitride, diamond and graphite. Aluminum alloy is the preferred material.

Figure 1:
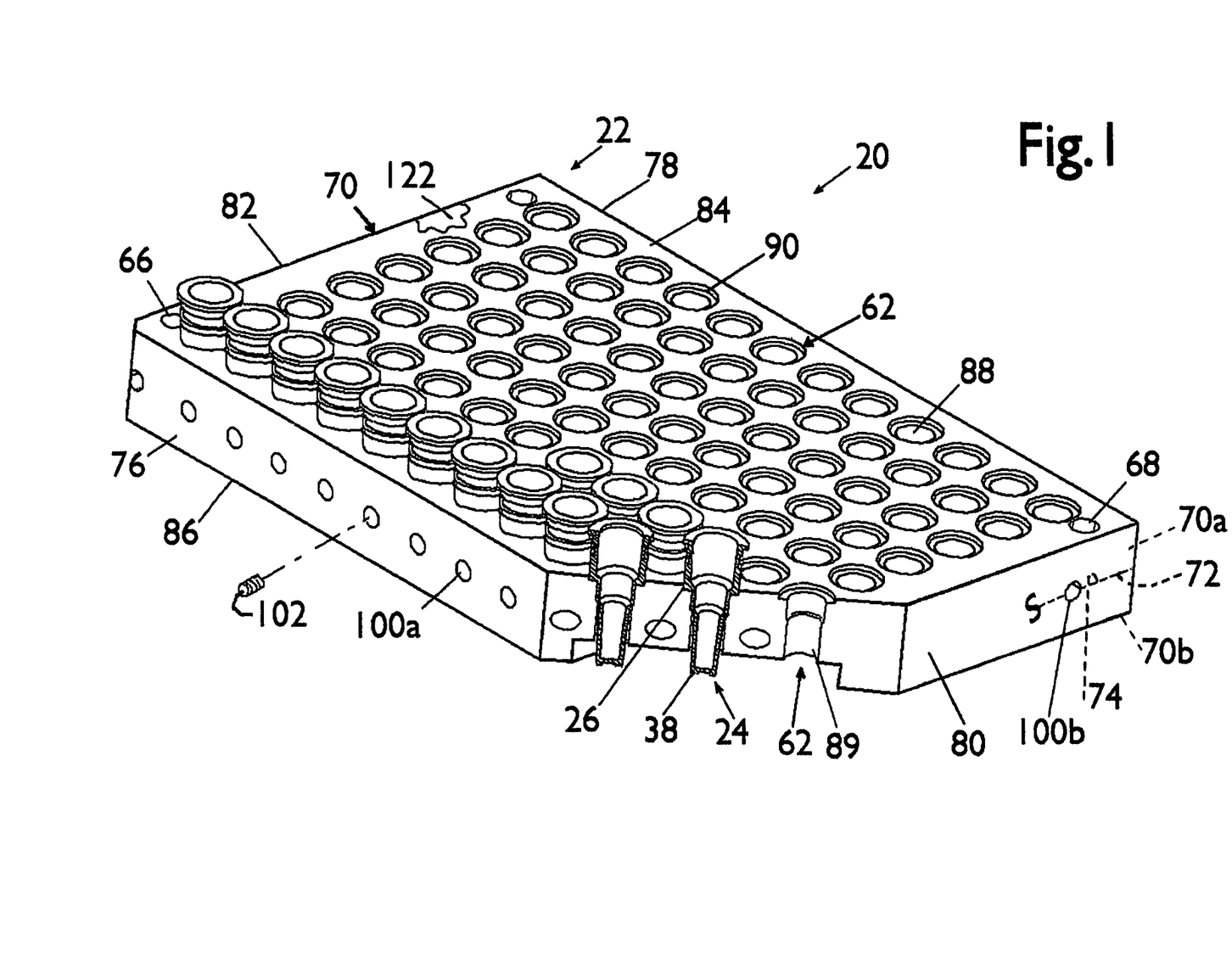
FIG. 1 is a perspective view, with a part cut away, showing a heat removal module having receiving stations for supporting a plurality of reaction vessels, in accordance with certain principles of the invention.
Figure 5:
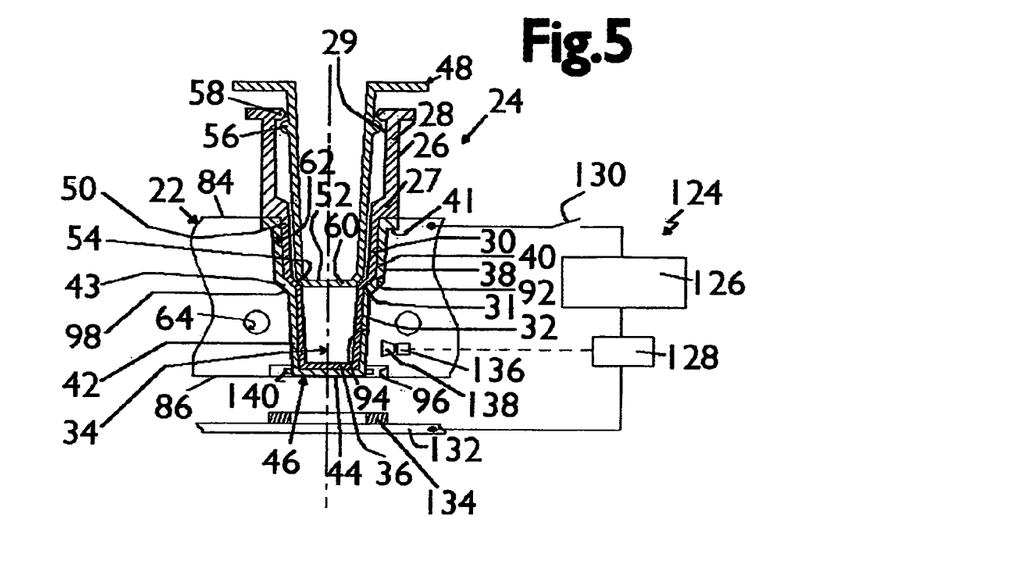
FIG. 5 is a partial sectional view showing a single receiving station of the heat removal module of FIG. 1, with a single reaction vessel within the receiving station, in accordance with certain principles of the invention.

As shown in FIGS. 1 and 5, the module 22 is structured to support a reaction vessel 24 (hereinafter "the vessel") of the type commonly used in biological and chemical reaction testing of various reagents. The vessel 24 is formed with an electrically non-conductive inner casing 26, or electrically insulative liner, and includes an upper larger section 28 having an upper funnel opening 29 of the vessel, through which reagents are introduced into the vessel. The inner casing 26 of the vessel 24 further includes a transition section 27, an intermediate mid-size section 30, a transition section 31, and a lower smaller section 32, which forms a reaction portion, such as a reaction chamber 34, or cavity, with each section having a slightly tapered wall to form the inner casing in a stepped, funnel-like shape with a closed bottom at a base 36 of the vessel to form a floor of the reaction chamber 34. The reaction portion or chamber 34 is formed with a length of eight millimeters and a mean bore of two and one-half millimeters. The upper section 28, the intermediate section 30, and the lower section 32 of the inner casing 26 are formed with successively smaller diameters, with the upper opening 29 forming the only opening into the vessel 24. Further, the vessel 24 includes an electrically conductive outer casing 38, which includes an upper larger section 40 formed with a contact ledge 41 at an upper portion of the larger section. The outer casing further includes a lower smaller section 42, with a transition section 43 between the upper larger section and the lower smaller section, and a base 44, which conform to, and are integrally joined with, outer surfaces of the intermediate section 30, the transition section 31, the lower section 32, and the base 36, respectively, of the funnel-like shape of the inner casing 26. The base 36 of the inner casing and the base 44 of the outer casing 38 combine to form a closed base 46 of the vessel 24. The outer casing 38 of the vessel 24 has an outside diameter of approximately four millimeters and a length of three millimeters. The upper section 28 of the vessel 24, formed by the inner casing 26, is a funnel portion of the vessel and has a mean outside diameter of six millimeters and a length of seven millimeters. The vessel 24 has a wall thickness of generally three tenths of a millimeter.

The inner casing 26 and the outer casing 38 of the vessel 24 are formed by a two-shot molding process, in which the two layers are formed of different polymers. The inner casing 26 is composed of electrically non-conductive polypropylene, which provides an optimal surface for contact with the reagents in the reaction chamber 34 as anticipated in many biological reactions, and also provides good thermal coupling between the outer casing 38 and the reagents located within the reaction chamber. The outer casing 38 is an electrically conductive polypropylene (ECP), and contains carbon fiber and carbon black, which heats when a voltage differential is applied thereacross, resulting in current flow therethrough, whereby an even and predictable heating of the reaction chamber 34 occurs. The carbon fibers are milled carbon fibers so that the fibers are of optimal length for the manufacturing process of the vessel 24. Also, the outer casing 38 varies in thickness so that the heat applied to the contents is even.

In preparation for use of the vessel 24, a sample of a reagent is deposited into the vessel 24 through the upper opening 29, and settles onto the floor of the base 36. A lid 48, having a tapered nose 50, is inserted into the opening 29 of the vessel 24, and is tapered to conform to a tapered inner surface of the intermediate section 30 of the inner casing 26. A base 52 of the lid 48 eventually rests on a mating tapered transition surface 54, at a juncture between the intermediate section 30 and the lower section 32. Further, an outward rib 56 formed on an external surface of the lid 48, near the top thereof, is snapped below an inward ledge 58 formed at the top of the inner casing 26. With this arrangement, the engagement of the rib 56 below the ledge 58 urges the base 52 of the lid 48 firmly into engagement with the transition surface 54 to lock the lid in place as shown in FIG. 5, and to effectively seal the opening of the reaction chamber 34. The base 52 of the lid 48 is formed with a sealed translucent or transparent window 60, which allows optical interrogation of the reaction of the heated reagent sample within the reaction chamber 34.

Figure 2:
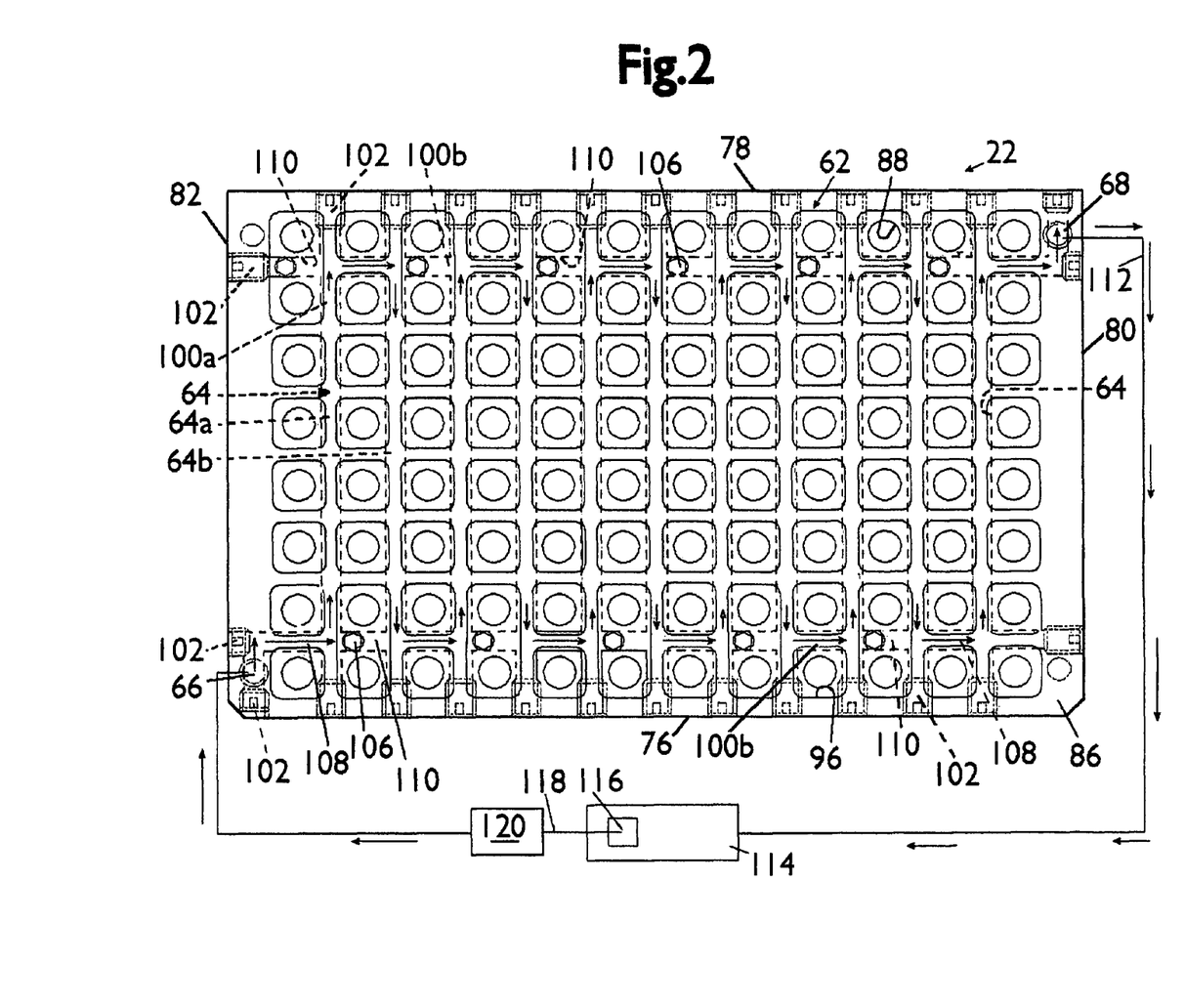
FIG. 2 is a plan view of a bottom of the heat removal module of FIG. 1, in accordance with certain principles of the invention.

As illustrated in FIGS. 1 through 5, the module 22 is formed with at least one receiving station 62 (hereinafter "the station") to receive snugly the reaction vessel 24 in such a manner that good thermal conductivity contact is created between the module and the vessel. As shown in FIG. 2, the module 22 is also formed internally with a channel 64, which extends between an entry port 66 and an exit port 68 formed in the module. The channel 64 extends through the module 22 in a labyrinth configuration, and in a serpentine fashion, as described below. A coolant liquid is fed into the entry port 66, flows through the channel 64 adjacent the station 62 and any vessel 24 located in the station, and exits through the exit port 68. As the coolant liquid flows through the channel 64, the liquid passes adjacent the station 62 and the vessel 24 therein, and cools and maintains the vessel at a desired temperature. The coolant liquid may be water, and is preferably deionizsed water, with an antioxidant added thereto, of the type referred to commercially as FluidXP+, which is available from Integrity PC Systems & Technologies, Inc. of Riverdale, Calif., USA.

In the preferred embodiment, the module 22 is formed as a unitary structure, in the form of a single block 70 (FIG. 1). As represented partially by dashed lines in FIGS. 1 and 4, the module 22 could be formed as a unitary structure, including a first mating plate 70a, having a first interfacing surface 72, which is in facing engagement with a second mating surface 74 of a second mating plate 70b, without departing from the spirit and scope of the invention.

Referring to FIG. 1, the block 70 of the module 22 is formed with a first side surface 76, and a second side surface 78 spaced from, and parallel with, the first side surface. The module 22 is further formed with a third side surface 80, and a fourth side surface 82 spaced from, and parallel with, the third side surface, with the surfaces 80 and 82 being perpendicular with the surfaces 76 and 78 to form the block 70 in a rectangular configuration. The block 70 is also formed with a top surface 84 and a bottom surface 86. A plurality of the receiving stations 62 are formed through the block 70, from the top surface 84 to the bottom surface 86. As shown in FIG. 1, typically, the plurality of receiving stations 62 are arranged in a twelve by eight matrix of ninety six receiving stations, referred to as a standard microtiter array, with the vessels 24 placed therein being referred to as microtiter vessels. The ninety-six vessels 24, arranged in the twelve by eight array are located at nine millimeter centers. The module 22 can be formed with a single receiving station 62, or with any number of receiving stations, including a number of stations based on integer multiples of ninety six, without departing from the spirit and scope of the invention.

Figure 4:
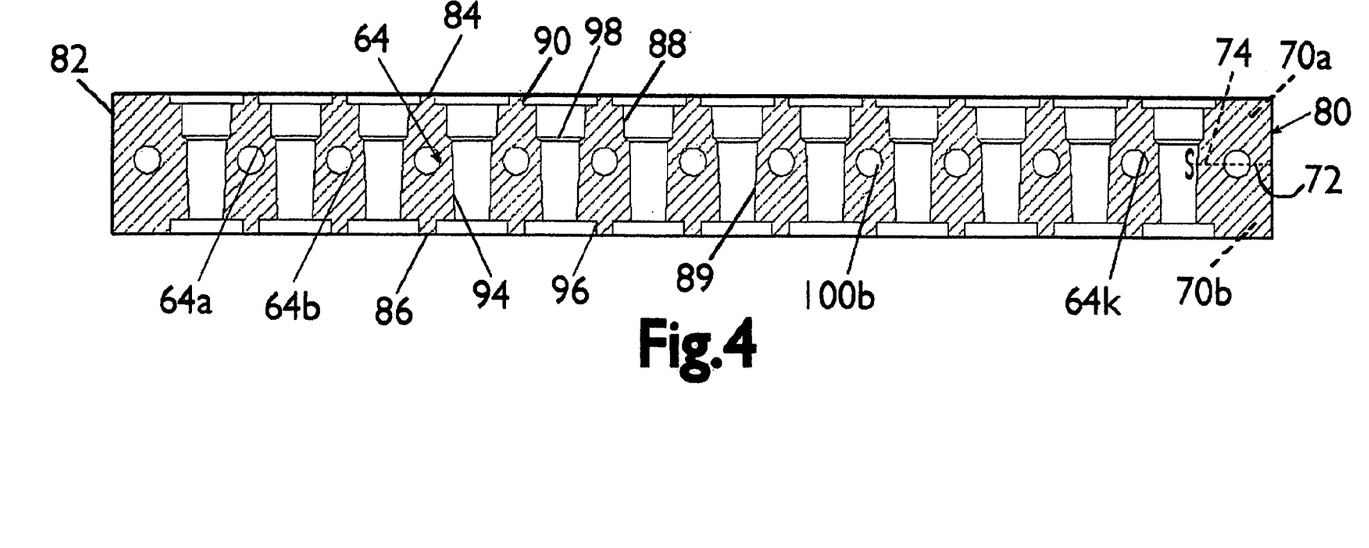
FIG. 4 is a sectional side view of the heat removal module of FIG. 1 showing the receiving stations and a portion of the labyrinth channel, in accordance with certain principles of the invention.

Referring to FIG. 4, each receiving station 62 is formed with a receptor passage 88, which extends through the module 22, from the top surface 84 to the bottom surface 86. Each passage 88 includes a top contact recess 90 formed in the top surface 84 at an entry port of the passage, an upper section 92, a lower section 94, and a bottom recess 96. The upper section 92 is formed with a larger tapering diameter than a tapering diameter of the lower section 94 at an exit port of the passage. A transition surface 98 is formed at a juncture between the upper section 92 and the lower section 94, with the upper section and the lower section being tapered to conform to the tapers of the upper section 40 and lower section 42, respectively, of the outer casing 38 of the vessel 24. The receptor passage 88 of each receiving station 62 is formed with a wall 89, or wall surface, which extends between the top contact recess 90 and the bottom recess 96. The flow passages 100a and 100b, and thereby the channel 64, are formed by a three millimeters bore size.

As shown in FIGS. 1, 2, 3 and 4, in the forming of the channel 64, a plurality of parallel, spaced flow passages 100a are formed, by drilling or other methods, through the module 22, in a common plane, from the first side surface 76 to the second side surface 78, with each of the flow passages having ports in the first side surface and the second side surface. As shown in FIG. 2, two parallel, spaced flow passages 100b are formed, by drilling or other methods, through the module 22, in the common plane, from the third side surface 80 to the fourth side surface 82, with the flow passages 100a intersecting each of the flow passages 100b, in the common plane, to normally provide communication amongst the flow passages 100a and 100b. With respect to the flow passages 100b, the third side surface 80 and the fourth side surface 82 may be referred to as the first and second side surfaces, respectively, of those flow passages. A stopper 102, in the form of a set or grub screw, is inserted into, and secured within, each port of the flow passages 100a and 100b, which essentially seals the flow passages from communication with the exterior environment of the module 22, except through the entry port 66 and the exit port 68.

It is noted that, if the unitary structure of the module 22 is in the form of the above-described first mating plate 70a and the second mating plate 70b, portions of the flow passages 100a and 100b can be formed in the first interfacing surface 72 and the remaining portions formed in the second interfacing surface 74. when the two mating plates 70a and 70b are assembled together, the respective portions of the flow passages 100a and 100b will mate to form the complete flow passages.

Figure 3:
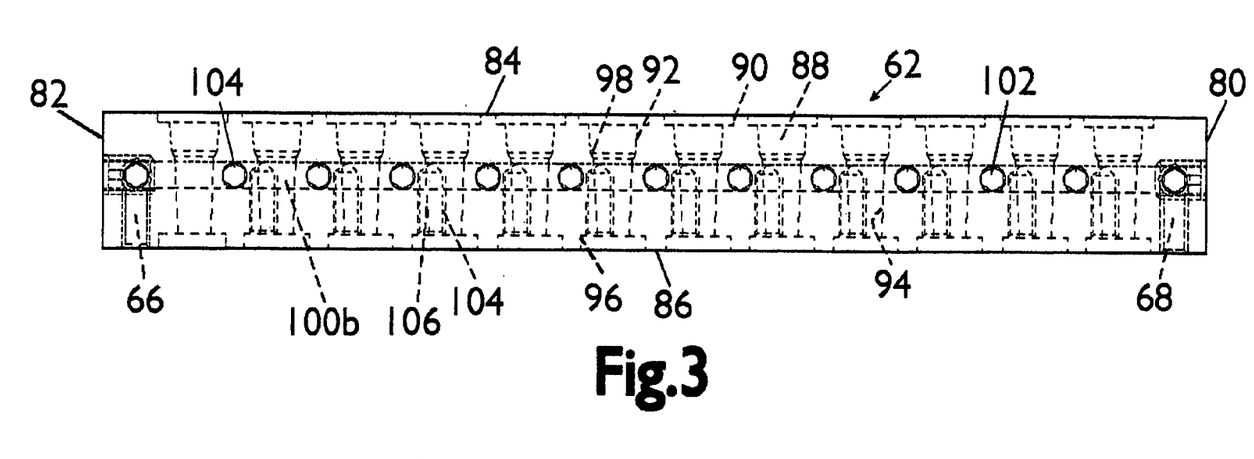
FIG. 3 is a side view of the heat removal module of FIG. 1, with dotted lines showing the location of the receiving stations and a portion of a labyrinth channel, in accordance with certain principles of the invention.
Figure 6:
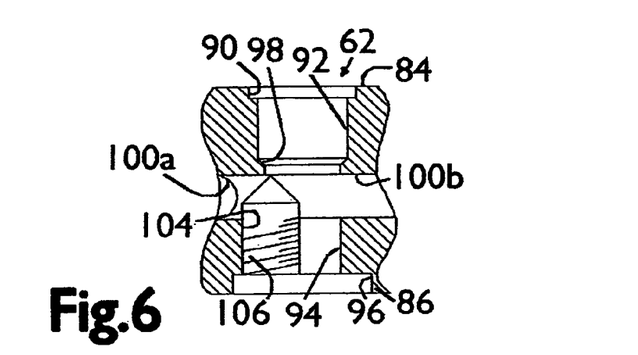
FIG. 6 is a partial sectional view showing the heat removal module of FIG. 1 with a stopper located to facilitate formation of the labyrinth channel, in accordance with certain principles of the invention.

Referring to FIGS. 2, 3 and 6, a plurality of selectively placed holes 104 are formed, by drilling or other methods, into the module 22, from the floor of the bottom recess 96, and into the flow passages 100b. A flow stopper 106, in the form of a set or grub screw, is secured within each of the holes 104, and extends into the respective passages 100b to preclude the flow of the coolant liquid through the respective blocked portions of the flow passages 100b. With this arrangement, the flow passages 100b are separated into alternating communicating portions 108, which communicate with the flow passages 100a, and alternating non-communicating portions 110, which are not in flow communications with the flow passages 100a. Portions of the flow passages 100a and 100b now provide a flow path in the labyrinth configuration to form the channel 64, and to force the coolant liquid to flow in the serpentine path.

Referring to FIG. 2, for purposes of describing the serpentine path, the flow passages 100a will be referred to as being arranged in a vertical orientation in the figure, and the flow passages 100b will be referred to as being arranged in a horizontal orientation in the figure. In actual use of the module 22, the common plane of the flow passages 100a and 100b is typically in a horizontal orientation, but could be in other orientations without departing from the spirit and scope of the invention. Also, in the description below, it is to be understood that the stoppers 102 preclude the outflow of the coolant liquid from any of the ports of the flow passages 100a and 100b.

The coolant liquid flows into the entry port 66, and horizontally into one of the communicating portions 108 of a lower one of the flow passage 100b. As the coolant liquid approaches the first intersection of the flow passages 100a and 100b, the liquid encounters the flow stopper 106 located in one of the non-communicating portions of the flow passage 100b, and is urged vertically upward into the flow passage 100a. As the coolant liquid reaches the vertically upper end of the flow passage 100a, the liquid is urged, and flows horizontally, into an upper one of the communicating portions of the flow passages 100b. As the liquid approaches the next intersection of the flow passages 100a and 100b, the liquid encounters the flow stopper located in one of the non-communicating portions of the flow passage 100b, and is urged vertically downward into the flow passage 100a. This pattern of vertically upward and vertically downward travel of the liquid is continued, in the serpentine path until the liquid reaches the exit port 68, and exits the module 22. With respect to the channel 64, the coolant liquid flows vertically upward through a vertical leg 64a of the channel, and vertically downward through a second vertical leg 64b. This flow pattern is continued until the liquid flows vertically upward through the last vertical leg 64k of the channel 64.

As further shown in FIG. 2, the coolant fluid exits the module 22 through the exit port 68, and flows into a return conduit 112, and eventually into a reservoir 114. A pump 116, within the reservoir pumps the coolant liquid from the reservoir 114 into an input conduit 118, where the liquid passes through a heater 120 to selectively preheat the liquid. The coolant liquid is then fed into the entry port 66 of the module 22, and continues through the serpentine path of the channel 64 as described above. With the labyrinth configuration, the coolant fluid is directed adjacent at least on side of each receiving station 62, and adjacent two sides of most of the receiving stations.

As noted above, the module 22 is formed of an electrically conductive material. The exposed surfaces of the module 22, including the walls 89 of the receiving station 62 and the bottom recesses 96, and excluding the top contact recesses 90, are coated with an electrically non-conducting or insulative material, as represented partially by a coating layer 122, shown in FIG. 1. The insulating of the exposed surfaces of the module 22, except for the top contact recesses 90, can be accomplished by anodizing such surfaces. The top contact recesses remain uncoated to provide electrical contact surfaces as described below.

Referring again to FIG. 5, an electrical system 124, for heating the reaction vessel 24, and controlling the temperature thereof during the reaction process, includes an electrical power source 126, a heat controller 128, a switch 130, a PCB 132 and a contact 134 mounted on the PCB. To provide an electrical path for current flow to heat the reaction chamber 34, the electrical system 124 further includes the conductive outer casing 38 of the vessel 24, and the electrically conductive material of the module 22, which includes the top contact recess 90. Also, one side of the electrical power source 126 is connectable, through the switch 130, to a contact formed on the electrically conductive module 22. The other side of the electrical power source 126 is connected, through the heat controller 128 to a conductive terminal on the PCB 132, with the terminal being electrically connected to the contact 134 through a conductive path on the PCB.

The heat controller 128 is responsive to an output from a heat sensor 136, which is positioned adjacent the reaction chamber 34 to constantly monitor the temperature in the chamber. If an infrared sensor is used as a heat sensor, a heat guide 138 may be employed to collect radiated from the surface of the vessel 24, and guide the radiated heat to the infrared sensor. A toroid 140 may be located about the base 46 of the vessel 24 to accommodate a temperature sensing device, which could be a thermal contacting type, for example a thermistor, or a remote sensor, for example a thermocouple type.

With respect to the following description of the use of the apparatus 20, the description will be with respect to a single vessel 24 and a single receiving station 62 within the module 22, it being understood that the same procedure will be followed with respect to use of two or more of the vessels in two or more respective receiving stations.

When the apparatus 20 is to be used for the reaction process, the electrical system 124 is established as described above. A sample of the reagent is deposited in the vessel 24, and the reagent settles on the floor of the reaction chamber 34. The vessel 24, with the deposited reagent, is then placed into the receptor passage 88 of the receiving station 62 of the module 22. It is noted that the reagent could be placed in the vessel 24 after placement of the vessel in the receiving station 62, without departing from the spirit and scope of the invention. As the vessel 24 is placed into the receptor passage 88, the contact ledge 41 of the conductive outer casing 38 of the vessel is moved into firm electrical contact with the uncovered top contact recess 90 of the module 22. At the same time, the base 46 of the vessel 24 extends into the insulated bottom recess 96 of the receiving station 62 in the manner illustrated in FIG. 5. Relative movement is effected between the module 22 and the PCB 132 to move the PCB-mounted contact 134 into electrical contact engagement with the exposed base 46 of the vessel 24, The lid 48 is then placed into the funnel-shaped opening of the inner casing 26 of the vessel 24 to seal the reaction chamber 34 in the manner described above, with the lid window 60 in place for optical interrogation of the reagent sample during the reaction process. It is noted that the lid window 60 is located well within an intermediate portion of the outer casing 38 to heat the window. This arrangement reduces the possibility of condensation forming on the window 60, and thereby allows for accurate and reproducible optical monitoring of the reactions occurring in the reaction chamber 34 of the vessel.

Typically, in biological or chemical reactions involving thermo cycling, it is necessary to precisely control the temperature range between lower and upper temperature levels, where the lower temperature is higher than the ambient. Accordingly, the apparatus 20 for effecting the reaction of the reagent within the reaction chamber 34 utilizes the module 22 in accordance with certain principles of the invention by providing the heater 120 for preheating the coolant liquid to the desired temperature. This arrangement has an added advantage of preventing condensation from forming on the exterior of the module 22. In this context, pre-heated coolant liquid is pumped through the channel 64, in preparation for the initiation of a heating cycle to apply heat to the reaction chamber 34.

Thereafter, the switch 130 is closed to complete the electrical circuit, whereby current flows through the outer casing 38, between the contact ledge 41 and the base 46 thereof, and the reaction chamber 34 is heated to initiate the reaction process. During the reaction process, the heat sensor 136 feeds temperature data to the heat controller 128, which responds to the data to increase, decrease, or hold steady, the level of current flowing in the outer casing 38 of the vessel 24, in accordance with preset standards.

Figure 7:
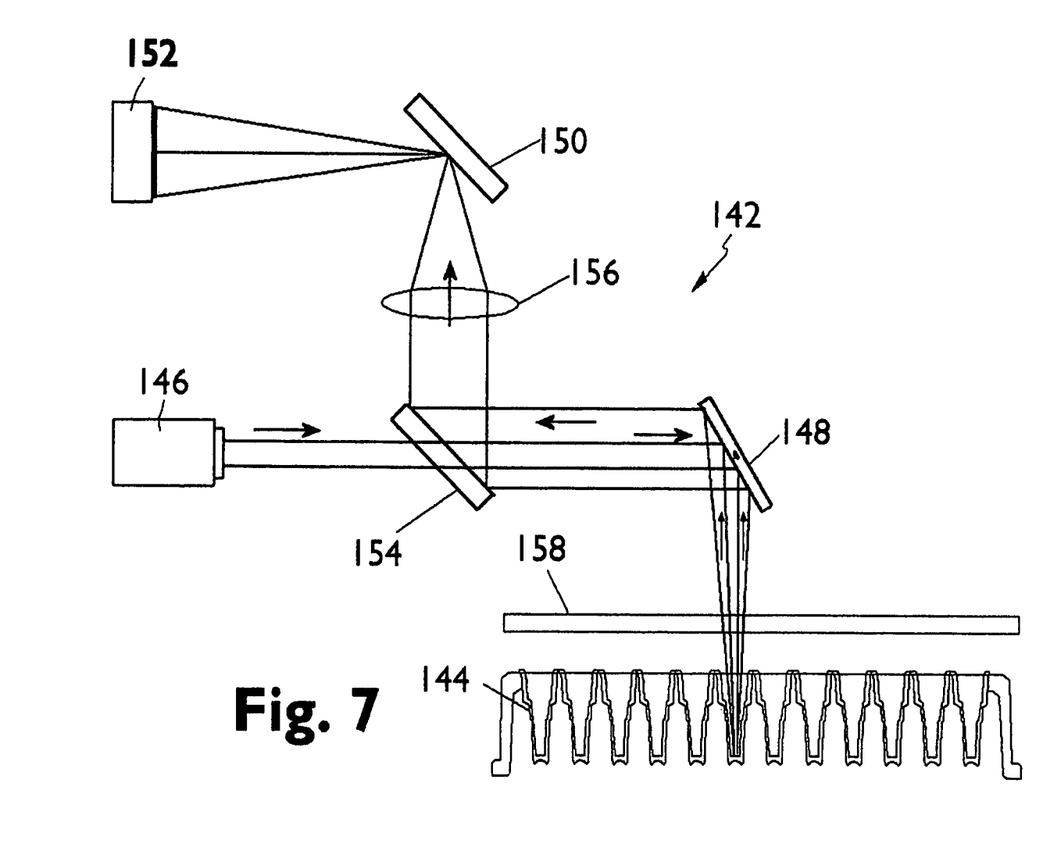
FIG. 7 is a diagram of a first optical interrogation system, in accordance with certain principles of the invention.

As illustrated in FIG. 7, an optical monitoring system 142, hereinafter referred to as "the optical system," is provided as a part of the apparatus 20, wherein a representation of a plurality of receiving stations is shown, with each station receiving a reaction vessel 144 in which a reaction may take place. The system comprises at least one light source 146, a scanning apparatus 148 for directing the light to the reaction vessels 144 in the receiving stations and for receiving radiation emitted by the reaction vessels and directing the radiation via a diffraction grating 150 to a multi-anode photomultiplier tube assembly 152 operating in a photon counting mode. A foraminous mirror 154 contains a small opening at forty-five degrees to the plane of the mirror, permitting laser light to pass through it to the vessels 144. The majority of diverging emitted light from the vessels 144 is reflected to the diffraction grating 150, since at this point the emitted light beam is of much greater diameter than the small opening.

The multi-anode photomultiplier tube assembly 152 includes a multi-anode photomultiplier tube (MAPMT) with a 32 pixel array over which radiation from around 510 to 720 nm is dispersed. Radiation emitted by the reaction vessel 24 contents is dispersed over the pixels of the MAPMT by the diffraction grating 150 such that the wavelength range of the radiation impinging on a photocathode of the MAPMT correlates with the position of the photocathode in the MAPMT.

The light source 146 is a diode pumped solid state laser (DPSS Laser) which is smaller and lighter than conventional gas lasers typically used in optical monitoring systems.

The scanning apparatus 148 includes one or more planar rotatable mirrors, for clarity only one such mirror is illustrated. These are motor driven and controlled by means which are omitted from the drawings for clarity. The system of mirrors can be configured to direct the light from the laser to any receiving station. Radiation emitted is returned to the foraminous mirror 154 which reflects the majority of the emitted radiation through a lens 156 which focuses the radiation upon the diffraction grating 150. A Fresnel lens 158 is interposed between the rotatable mirrors, e.g. mirror 148, and the receiving stations to ensure verticality of the light entering each reaction vessel 144.

Figure 8:
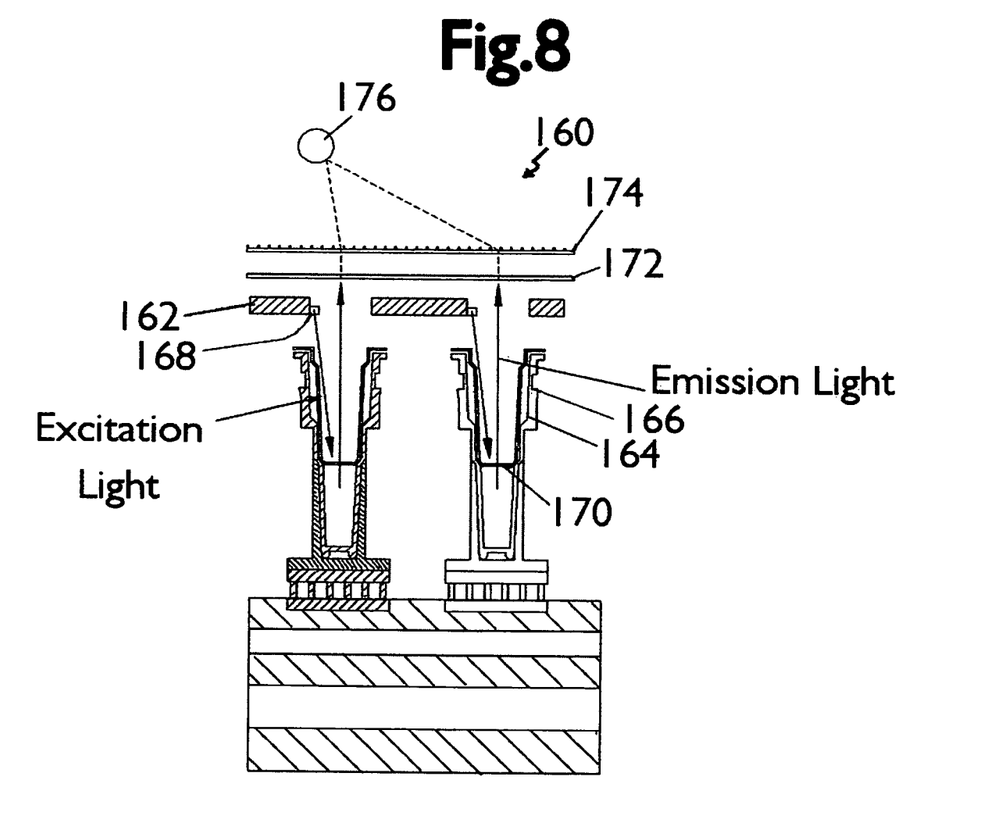
FIG. 8 is a diagram of a second optical interrogation system, in accordance with certain principles of the invention.

Referring to FIG. 8, an optical arrangement 160, which is an alternate embodiment of the optical system 142, includes a PCB 162, located above a pair of spaced lids 164, positioned over respective reaction vessels 166. An array of LEDs 168 are mounted on the PCB 162, and are selected to emit light at 470 nm and arranged for the light thereof to be directed through a window 170, or translucent portion, of each of the lids 164. An optical filter 172 is located above a plurality of small openings 174 formed through the PCB 162, whereby only emission spectra and not excitation spectra is allowed to pass. A Fresnel lens 174 directs the light emerging from the vessels onto a detector 176 in the form of a photomultiplier tube.

In general, the above-identified embodiments are not to be construed as limiting the breadth of the present invention. Modifications, and other alternative constructions, will be apparent which are within the spirit and scope of the invention as defined in the appended claims.

What is claimed is:

1. An apparatus for biological or chemical reactions, which comprises:
   a heat removal module adapted to receive one or more reaction vessels in such a manner as to create thermal conductivity between the heat removal module and each of the one or more reaction vessels in a thermal cycling process;
   the heat removal module being formed of a thermally conductive material; and
   a channel formed in the heat removal module and adapted for the flow of a coolant liquid therethrough adjacent each of the one or more reaction vessels;
   the channel having an inlet port formed at a first exterior location of the heat removal module and an outlet port formed at a second location of the heat removal module spaced from the the first exterior location to facilitate the flow of the coolant liquid through the channel from the inlet port to the outlet port;
   a coolant liquid passage extending between the outlet port and the inlet port to facilitate the continuous circulating flow of the coolant liquid through the channel and the passage; and
   a heater located in the coolant-liquid passage to heat the coolant liquid to a prescribed temperature for establishing a prescribed-temperature environment throughout the heat removal module in which each of the one or more reaction vessels can be thermally cycled independently of the thermal cycling of the remaining one or more reaction vessels to effect an independent biological or chemical reaction within each of the one or more reaction vessels.

2. The apparatus as set forth in claim 1, wherein the coolant liquid is water.

3. The apparatus as set forth in claim 2, wherein the water is deionized water with an antioxidant addition.

4. The apparatus as set forth in claim 1, which further comprises:
   the heat removal module formed with a one or more receiving stations for receipt therein of the one or more reaction vessels.

5. The apparatus as set forth in claim 1, which further comprises:
   the heat removal module formed with one or more receiving stations in a prescribed array for receipt therein of one or more reaction vessels.

6. The apparatus as set forth in claim 1, which further comprises:
   the channel extending between the entry port and the exit port in a serpentine path.

7. The apparatus as set forth in claim 1, which further comprises:
   the heat removal module formed as a unitary structure of the thermally conductive material.

8. The apparatus as set forth in claim 1, which further comprises:
   the heat removal module formed with one or more receiving stations for receipt therein of the one or more reaction vessels; and
   the channel being formed in a labyrinth configuration with each of a plurality of spaced portions thereof being located adjacent at least a portion of a respective one of the one or more receiving stations such that the coolant liquid flows adjacent at least a portion of each of the one or more receiving stations, and any reaction vessel which may be located in the respective one of the one or more receiving stations.

9. The apparatus as set forth in claim 8, which further comprises:
   the labyrinth configuration of the channel being arranged so that the coolant liquid flows adjacent at least two spaced portions of at least one receiving station of the one or more receiving stations, and two spaced portions of any reaction vessel which may be located in the at least one receiving station.

10. The apparatus as set forth in claim 7, which further comprises:
    the unitary structure of the heat removal module formed as a single block of the thermally conductive material.

11. The apparatus as set forth in claim 8, which further comprises:
    a plurality of flow passages formed through the heat removal module to facilitate the forming of the channel.

12. The apparatus as set forth in claim 8, which further comprises:
    the heat removal module being formed as a single block.

13. The apparatus as set forth in claim 1, wherein the heat removal module further comprises:
    each of one or more receiving stations formed by a receptor passage which extends between and through a first major surface of the heat removal module and a second major surface of the heat removal module; and
    the receptor passage is formed with a wall.

14. The apparatus as set forth in claim 13, which further comprises:
    the wall being formed in a configuration which generally matches a configuration of an external surface of at least a portion of the reaction vessel to be received within the receptor passage.

15. The apparatus as set forth in claim 13, which further comprises:
the wall of the receptor passage being electrically insulated to preclude electrical contact with any portion of the reaction vessel to be located within the receptor passage.

16. The apparatus as set forth in claim 1, which further comprises:
an external surface of the heat removal module being coated with a layer of an electrically insulative material.

17. The apparatus as set forth in claim 1, which further comprises:
an external surface of the heat removal module being anodized.

18. The apparatus as set forth in claim 1, which further comprises:
the heat removal module being structured for use with a reaction vessel having a wall thickness of generally 0.3 mm.

19. The apparatus as set forth in claim 1, which further comprises:
an optical monitoring means for monitoring the progress of a reaction within the one or more reaction vessels.

20. The apparatus as set forth in claim 19, wherein the optical monitoring means comprises:
a laser source;
means for directing a laser beam into the one or more reaction vessels, and
a multi-anode photomultiplier tube for detecting emitted light resulting from a reaction occurring within each of the one or more reaction vessels.

21. The apparatus as set forth in claim 1, wherein the heat removal module further comprises:
one or more receiving stations in the heat removal module for receiving the one or more reaction vessels;
means for monitoring the reaction in the one or more reaction vessels; and
a vessel temperature sensor located at the receiving station.

22. The apparatus as set forth in claim 21, which further comprises:
the vessel temperature sensor is selected from the group consisting of an infra-red detector, a thermistor, and a thermopile sensor.

23. The apparatus as set forth in claim 21, which further comprises:
a heat guide arranged to guide heat radiated from a surface of the reaction vessel onto the vessel temperature sensor.

24. A heat removal module for use in conducting biological or chemical reactions, which comprises:
one or more receiving stations formed in the heat removal module for receiving one or more reaction vessels in such a manner as to create thermal conductivity between the heat removal module and the one or more reaction vessels in a thermal cycling process;
the heat removal module being formed of a thermally conductive material,
a channel formed in the heat removal module for facilitating the flow of a coolant liquid therethrough adjacent each of the one or more reaction vessels;
the channel having an inlet port formed at a first exterior location of the heat removal module and an outlet port formed at a second location of the heat removal module spaced from the the first exterior location to facilitate the flow of the coolant liquid through the channel from the inlet port to the outlet port;
a coolant liquid passage extending between the outlet port and the inlet port to facilitate the continuous circulating flow of the coolant liquid through the channel and the passage; and
a heater located in the coolant-liquid passage to heat the coolant liquid to a prescribed temperature for establishing a prescribed-temperature environment throughout the heat removal module in which each of the one or more reaction vessels can be thermally cycled independently of the thermal cycling of the remaining one or more reaction vessels to effect an independent biological or chemical reaction within each of the one or more reaction vessels.

* * * * *